(12) United States Patent
Pip et al.

(10) Patent No.: US 6,540,949 B2
(45) Date of Patent: Apr. 1, 2003

(54) BIORIENTED POLYETHYLENE FILM WITH A HIGH WATER VAPOR TRANSMISSION RATE

(75) Inventors: Hans Joachim Pip, Arlon (BE); Rhonda Rogers Agent, Rochester, NY (US)

(73) Assignee: ExxonMobil Oil Corporation, Fairfax, VA (US)

( * ) Notice: Subject to any disclaimer, the term of this patent is extended or adjusted under 35 U.S.C. 154(b) by 148 days.

(21) Appl. No.: 09/837,673

(22) Filed: Apr. 18, 2001

(65) Prior Publication Data

US 2001/0017431 A1 Aug. 30, 2001

Related U.S. Application Data

(63) Continuation of application No. 09/079,807, filed on May 15, 1998, now abandoned.

(51) Int. Cl.[7] ............................................... B29C 47/06
(52) U.S. Cl. ........................ 264/172.19; 264/173.11; 264/290.2; 428/516
(58) Field of Search .................. 264/172.19, 173.11, 264/171.1, 212, 41, 288.8, 290.2; 428/516

(56) References Cited

U.S. PATENT DOCUMENTS

| | | | | |
|---|---|---|---|---|
| 4,472,328 A | * | 9/1984 | Sugimoto et al. .............. 264/41 |
| 4,777,073 A | * | 10/1988 | Sheth .......................... 428/155 |
| 4,814,124 A | * | 3/1989 | Aoyama et al. ............... 264/41 |
| 4,929,303 A | | 5/1990 | Sheth .......................... 156/209 |
| 5,055,338 A | * | 10/1991 | Sheth et al. .................. 428/155 |
| 5,084,352 A | * | 1/1992 | Percec et al. ................ 428/412 |
| 5,885,721 A | | 3/1999 | Su et al. ..................... 428/516 |
| 5,891,555 A | | 4/1999 | O'Brien ...................... 428/213 |

FOREIGN PATENT DOCUMENTS

WO    WO94/14606    7/1994

OTHER PUBLICATIONS

Library of Congress Cataloging in Publication Data: The Wiley Encyclopedia of Packaging Technology, Marilyn Bakker, Editor–in–Chief, Copyright 1986 by John Wiley & Sons, Inc. title: Film, High Density Polyethylene (pp. 313–315) and title Polyethylene, High Density (pp. 514–529).

* cited by examiner

Primary Examiner—Mark Eashoo
(74) Attorney, Agent, or Firm—Rich E. James; Keith A. Bell

(57) ABSTRACT

Methods of producing polyethylene films having a desired water vapor transmission rate (WVTR) are provided. The methods include casting a polyethylene sheet which has a base layer of a polyethylene and a cavitating agent, and at least one layer of a WVTR-controlling material, and subsequently biaxially orienting the sheet to yield a film having the desired WVTR. The base layer has a porous microstructure and a WVTR substantially higher than the desired WVTR.

11 Claims, 1 Drawing Sheet

BIORIENTED POLYETHYLENE FILM WITH A HIGH WATER VAPOR TRANSMISSION RATE

This application is a continuation of U.S. application Ser. No. 09/079,807 filed on May 15, 1998 now abandoned.

BACKGROUND OF THE INVENTION

The invention relates to methods for preparing polymer films. Specifically, the invention relates to methods of preparing bioriented polyethylene films having high water vapor transmission rates (WVTR).

Generally, in the preparation of a film from granular or pelleted polymer resin, the polymer is first extruded to provide a stream of polymer melt, and then the extruded polymer is subjected to the film-making process. Film-making typically involves a number of discrete procedural stages, including melt film formation, quenching, and windup. For a general description of these and other processes associated with film-making, see K R Osborn and W A Jenkins, *Plastic Films: Technology and Packaging Applications,* Technomic Publishing Co., Inc., Lancaster, Pa. (1992).

An optional part of the film-making process is a procedure known as "orientation." The "orientation" of a polymer is a reference to its molecular organization, i.e., the orientation of molecules relative to each other. Similarly, the process of "orientation" is the process by which directionality (orientation) is imposed upon the polymeric arrangements in the film. The process of orientation is employed to impart desirable properties to films, including making cast films tougher (higher tensile properties). Depending on whether the film is made by casting as a flat film or by blowing as a tubular film, the orientation process requires substantially different procedures. This is related to the different physical characteristics possessed by films made by the two conventional film-making processes: casting and blowing. Generally, blown films tend to have greater stiffness, toughness and barrier properties. By contrast, cast films usually have the advantages of greater film clarity and uniformity of thickness and flatness, generally permitting use of a wider range of polymers and producing a higher quality film.

Orientation is accomplished by heating a polymer to a temperature at or above its glass-transition temperature ($T_g$) but below its crystalline melting point ($T_m$), and then stretching the film quickly. On cooling, the molecular alignment imposed by the stretching competes favorably with crystallization and the drawn polymer molecules condense into a crystalline network with crystalline domains (crystallites) aligned in the direction of the drawing force. As a general rule, the degree of orientation is proportional to the amount of stretch, and inversely related to the temperature at which the stretching is performed. For example, if a base material is stretched to twice its original length (2:1) at a higher temperature, the orientation in the resulting film will tend to be less than that in another film stretched 2:1 but at a lower temperature. Moreover, higher orientation also generally correlates with a higher modulus, i.e., measurably higher stiffness and strength. Further, as a general rule, higher orientation correlates with lower WVTR values for films.

Previously, high WVTR values have been difficult to achieve with polyolefin films. Typically, film production methods aim to lower WVTR values for polyolefin films that have inherently low WVTR values compared to traditional wrapping materials such as cellulose films or paper.

Accordingly, it is one of the purposes of this invention, among others, to produce bioriented polyethylene films having high WVTR values, by providing an economical and relatively uncomplicated method of making polyethylene films that imparts superior characteristics to the films, without requirement for chemical additives such as cross-linking agents, and without requirement for supplemental processing steps such as irradiation of the film.

SUMMARY OF THE INVENTION

It has now been discovered that these and other purposes can be achieved by the present invention, which provides methods of producing polyethylene films having high water vapor transmission rates.

The methods provide for casting and then biaxially orienting a polyethylene sheet to obtain a film having a desired WVTR. The polyethylene sheet comprises a base layer comprising polyethylene and a cavitating agent, and at least one layer of a WVTR-controlling material coextensively adherent to a side of the base layer. The polyethylene sheet is biaxially oriented whereby there is provided a bioriented polyethylene film having the desired WVTR and whereby the base layer has a porous microstructure and a WVTR substantially higher than the desired WVTR.

Preferably, the polyethylene of the base layer is a medium density polyethylene (MDPE) or a high density polyethylene (HDPE). Further, it is preferable that the polyethylene in the base layer is provided in an amount sufficient to yield a base layer in the film having a thickness of from about 0.5 mil to about 2.0 mil (1 mil=0.001 inch=100 gauge), preferably about 0.85 mil (85 gauge) to about 1.10 mil (110 gauge).

In addition, it is preferable that the WVTR-controlling material is a MDPE or a HDPE, however, the WVTR-controlling material should not have a density greater than that of the polyethylene in the base layer. Further, it is preferable that the WVTR-controlling material is provided in an amount sufficient to yield a WVTR-controlling layer in the film having a thickness of from about 0.03 mil (3 gauge) to about 0.15 mil (15 gauge).

A preferred method of the present invention provides for producing a film from a polyethylene sheet having a three layer structure. In particular, a sheet having first and second layers of a WVTR-controlling material coextensively adherent to first and second sides of the base layer is provided for casting and then biaxial orienting.

Another preferred method of the present invention provides for producing a film from a polyethylene sheet having a five layer structure. In particular, the sheet provided for casting comprises a base layer interposed between two tie layers wherein the first tie layer is interposed between one side of the base layer and a first WVTR-controlling layer whereby the first tie layer is coextensively adherent to the base layer and the WVTR-controlling layer, and wherein the second tie layer is interposed between the other side of the base layer and a second WVTR-controlling layer whereby the second tie layer is coextensively adherent to the base layer and the WVTR-controlling layer.

Another method of the present invention provides for producing a film from a sheet having a structure wherein at least one tie layer is interposed between the base layer and a WVTR-controlling layer and the tie layer is coextensively adherent to the base layer and the WVTR-controlling layer. The WVTR-controlling layer comprises a WVTR-controlling material of preferably HDPE or MDPE. However, an alternative method includes provision for a WVTR-controlling layer comprising a WVTR-controlling material of an ethylene-propylene copolymer or an ethylene-propylene-butylene terpolymer wherein the tie layer comprises low density polyethylene (LDPE) or MDPE.

The present invention provides methods of producing polyethylene films having high WVTR values, opacity, high stiffness and resistance to humidity. The films also have excellent deadfold characteristics which make them well suited for packaging of foods in bag-in-box operations conducted on vertical, form, fill and seal (VFFS) machinery. These properties make these films an excellent alternative to paper or cellophane in applications where high WVTR and insensitivity of film to moisture are required.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein.

DETAILED DESCRIPTION OF THE PREFERRED EMBODIMENTS

Figure 1:
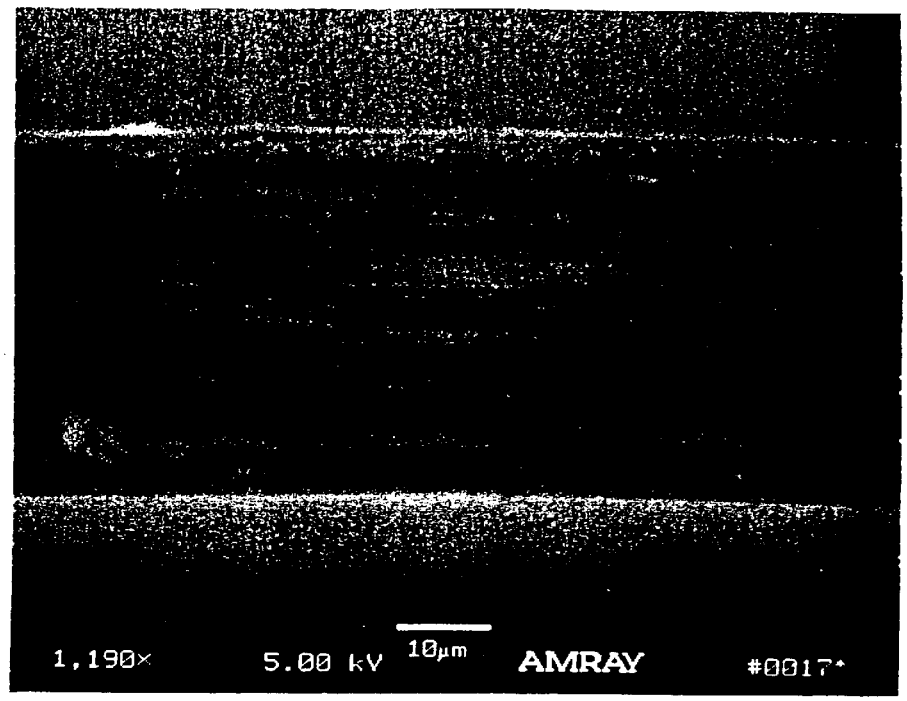
FIG. 1 is a scanning electron micrograph showing a cross-sectional view of a conventional cavitated bioriented polypropylene film.

The present invention provides methods of producing bioriented polyethylene films having a high WVTR. To practice the methods of the present invention, a polyethylene sheet comprising a core or base layer and at least one layer of a WVTR-controlling material should be provided. The polyethylene sheet is first cast and then biaxially oriented resulting in a film having a desired WVTR. The resulting film has a base layer having a porous microstructure and a substantially higher WVTR than the desired WVTR.

The base layer comprises a polyethylene and a cavitating agent. Preferably, the polyethylene is a HDPE or a MDPE. The amount of polyethylene provided in the base layer prior to casting the polyethylene sheet should be an amount sufficient to yield a base layer in the film having a thickness from about 0.5 mil to about 2.0 mil, preferably about 0.85 mil to about 1.10 mil (1 mil=0.001 inch=100 gauge). It should be noted that any thickness value provided herein does not account for additional thickness resulting from cavitation.

As the term HDPE is used herein, it is defined to mean an ethylene-containing polymer having a density of 0.940 or higher. (Density (d) is expressed as $g/cm^3$.) One particularly suitable HDPE for use with the methods of the present invention is the resin sold as M6211 by Equistar. Another particularly suitable HDPE is the resin sold as HDZ128 by Exxon. Other suitable HDPE resins include, for example, BDM 94-25 available from Fina Oil and Chemical Co., Dallas, Tex., and 19C and 19F available from Nova Corporation, Sarnia, Ontario, Canada.

The term "medium density polyethylene" (MDPE) as used herein is defined to mean an ethylene-containing polymer having a density of from about 0.926 to about 0.940. MDPE is readily available, e.g., Dowlex™ 2038 or Dowlex™ 2027A from The Dow Chemical Company.

As mentioned above, a cavitating agent is provided in the base layer. Such agents are typically added to the core or base layer prior to extrusion and are capable of generating voids (cavities) in the structure of the film during the film-making process. It is believed that small inhomogeneities introduced into the core layer by the cavitating agent result in points of weakness in the polyethylene sheet. The biaxial orienting step then induces tears in the core layer, causing cavitation in the processed film. The tears in the core layer vary in size and are formed not only horizontally, i.e., within or parallel to the plane of the film, but also in the vertical dimension or perpendicular to the plane of the film.

Any suitable cavitating agent may be used. One especially preferred cavitant which can be used to practice the methods of the present invention is calcium carbonate ($CaCO_3$). Other cavitating agents can also be used. Organic cavitating agents are also known, but are generally less preferred due to their limited operating temperature range. However, such organic cavitants may be useful if they are extremely finely divided and are either resistant to melt at operating temperatures or produce a suitable inhomogeneity in the polyethylene sheet. Cavitating agents can be included using methods known in the art, such as that described in Publication WO 9414606A1, incorporated herein by reference. Accordingly, in the methods of the invention in which a cavitating agent is employed, $CaCO_3$, polystyrene or other cavitants can be included in the base layer.

The percentage of cavitating agent included in the base layer may be dependent upon the desired WVTR. In particular, if a higher WVTR is desired, then more cavitating agent can be included in the base layer. Generally, the base layer can include from about 1 wt % to about 30 wt % of a cavitating agent. It is preferable, though, that the base layer comprise from about 3 wt % to about 10 wt % of a cavitating agent.

The WVTR-controlling layer includes a WVTR-controlling material. Any material that limits WVTR in the resulting film may be used. Given the typically small dimensions of the WVTR-controlling layer, the WVTR-controlling material will have a normalized WVTR lower than the net normalized WVTR of the film, and substantially lower than the normalized WVTR of the cavitated polyethylene base layer. Preferred WVTR-controlling materials include MDPE or HDPE. The WVTR-controlling material may have a density as great as that of the polyethylene in the base layer, but it should not have a density greater than that of the polyethylene in the base layer. The amount of WVTR-controlling material included in the WVTR-controlling layer prior to casting the polyethylene sheet should be an amount sufficient to yield a WVTR-controlling layer in the film having a thickness of from about 0.01 mil to about 0.25 mil, preferably from about 0.03 mil to about 0.15 mil.

A film is produced by the methods of the present invention using conventional casting apparatus. For example, cast extrusion is generally accomplished using a standard multi-roll stack system or a cast roll with an air cap (high velocity air applied to the outside of the sheet). Other casting apparatus is also useful, such as a cast roll and water bath system.

A polyethylene film prepared according to the present invention is biaxially oriented. Biaxial orientation is employed to evenly distribute the strength qualities of a film in the longitudinal or "machine direction" (MD) of the film and in the lateral or "transverse direction" (TD) of the film. Biaxial oriented films tend to be stiffer and stronger, and also exhibit much better resistance to flexing and folding forces, leading to greater utility in packaging applications.

Biaxial orientation can be conducted simultaneously in both directions, however, it is expensive to employ apparatus having the ability to do this. Therefore, most biaxial orientation processes use apparatus which stretches the film sequentially, first in one direction and then in the other. A typical apparatus will stretch a film in the MD first and then in the TD. The degree to which a film can be stretched is dependent upon factors including, for example, the polymer from which a film is made. For further discussion concerning high biorientation of polyethylene films, see U.S. Pat. No. 5,885,721 which is incorporated herein by reference.

A film according to the present invention is made from polyethylene and can be stretched to a relatively high degree. In particular, a film can be stretched in the MD to a degree of from about 5:1 to about 8:1 and in the TD to a degree of from about 6:1 to 15:1. Nevertheless, as a general rule with a film of this invention, the higher the degree of stretch in both the MD and the TD, the higher the WVTR in the resulting film. Another factor of the biaxial orienting step which can influence the WVTR in the resulting film is the stretch temperature. As shown below in EXAMPLE 3, the WVTR of a resulting film can be increased by biaxially orienting a film at a lower stretch temperature.

Several embodiments of polyethylene films can be produced by the methods of the present invention. One exemplary embodiment of a film produced by the methods provided herein has a base layer of HDPE and $CaCO_3$. The base layer is interposed between two WVTR-controlling layers, each of which comprises MDPE. Sufficient amounts of HDPE, $CaCO_3$ and WVTR-controlling material are provided prior to casting the polyethylene sheet to yield a base layer of the film having a thickness from about 0.85 mil to about 1.10 mil and WVTR-controlling layers each having a thickness from about 0.03 mil to about 0.15 mil.

Another exemplary embodiment includes a base layer comprising MDPE and $CaCO_3$. The base layer herein is also interposed between two WVTR-controlling layers and a sufficient amount of MDPE and $CaCO_3$ is provided prior to casting of the polyethylene sheet to yield a base layer of the film having a thickness from about 0.85 mil to about 1.10 mil. A sufficient amount of WVTR-controlling material is also provided to yield WVTR-controlling layers having a thickness from about 0.03 mil to about 0.15 mil. The WVTR-controlling layers may be of the same or different materials as desired. This film may be preferable in some applications since it is less stiff and it creases less than films having a base layer including HDPE. In addition, this film has unidirectional tear properties in the machine direction.

Another exemplary embodiment is a five layer structure comprising a base layer of HDPE and $CaCO_3$. The base layer is interposed between two tie layers; each tie layer is coextensively adherent to one side of the base layer. Further, one of the tie layers is coextensively adherent to a first outer layer of a WVTR-controlling material and the other tie layer is coextensively adherent to a second outer layer of a WVTR-controlling material.

The tie layers of this five layer structure comprise MDPE or HDPE. Process conditions, though, may warrant using a tie layer comprising HDPE and $CaCO_3$ if further cavitation is desired. In addition, the two tie layers may be of the same or different materials as desired. The outer layers of this five layer structure comprise MDPE as the WVTR-controlling material. The result of casting and biaxially orienting a sheet having this five layer structure is a rigid and opaque film having a gloss of about 25% and paperlike characteristics.

Yet another exemplary embodiment is a five layer structure comprising a base layer of HDPE and $CaCO_3$. The base layer is interposed between two tie layers; each tie layer is coextensively adherent to one side of the base layer. Further, one of the tie layers is coextensively adherent to a first outer layer of a WVTR-controlling material and the other tie layer is coextensively adherent to a second outer layer of a WVTR-controlling material.

The tie layers of this structure comprise a low density polyethylene or a MDPE to assure good skin adhesion. The tie layers may be of the same or different materials as desired. The WVTR-controlling material of the first and second outer layers can be an ethylene-propylene copolymer or an ethylene-propylene-butylene terpolymer. The WVTR-controlling layers may be of the same or different materials as desired. The result of casting and biaxially orienting a sheet having this five layer structure is a film having a high gloss of 60% where the WVTR-controlling material is an ethylene-propylene copolymer or an ethylene-propylene-butylene terpolymer. In addition, the resulting five layer film is paperlike, opaque and rigid making it attractive for use in cigarette pack inner liners where it would replace a paper or metallized paper or a paper/aluminum foil laminate.

While these and other embodiments may be produced according to the methods of the present invention, it must be noted that several other film structures having multiple layers with varying compositions and thicknesses can be produced having a desired WVTR in accordance with the present invention.

The films of the present invention can be coated to improve wettability of the film, adhesion between layers and ink receptivity. Conventional treatments may be used to coat these films.

The films produced according to the methods of the present invention are useful in numerous applications, such as food packaging and in particular, in food packaging where high WVTR is desirable such as the packaging of cheese products. Additionally, these films are advantageous for use in cigarette pack inner liners, as overwrap for butter, chocolate, candy, etc., and as twistwrap.

The following examples are provided to assist in further understanding the invention. The particular materials and conditions employed are intended to be further illustrative of the invention and are not limiting upon the reasonable scope thereof.

A series of experiments were performed to illustrate features and advantages of the present invention. Several of the manufacturing conditions were common to each case. For example, a polyethylene sheet was cast at a temperature between 160–180 F. depending upon the thickness of the sheet, i.e., the caster temperature was higher for thicker sheets. In addition, orientation was performed using conventional orienting equipment in each case. Further, each film was stretched in the machine direction at a temperature about 245–250 F. and in the transverse direction at about 262 F.

EXAMPLE 1

Figure 2:
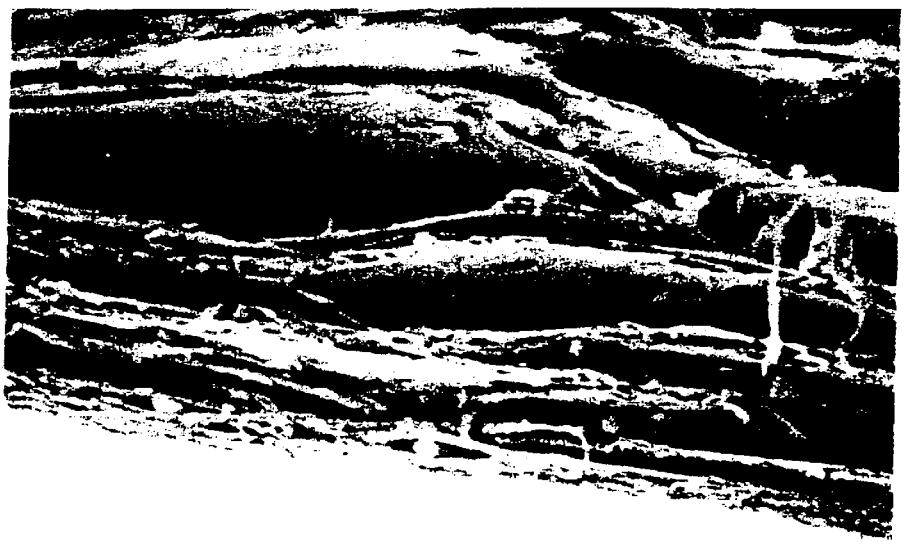
FIG. 2 is a scanning electron micrograph showing a cross-sectional view of a film prepared according to the present invention.

Referring now to FIGS. 1 and 2, cavitation of a film according to the present invention results in a surprising increase in the WVTR of the film. FIG. 1 is a scanning electron micrograph showing a cross-section through a conventional cavitated bioriented polypropylene (OPP) film. The core layer of the film contains 5% $CaCO_3$ as a cavitating agent. It is apparent that the cavitation introduced into this OPP film is exclusively within the plane defined by the film. Virtually no opening of the film in the dimension normal to the film plane (vertical) is evident. The physical structure of the cavitation in polypropylene is reflected in the minimal effect on the WVTR of the film. Typically, cavitation in OPP films increases WVTR by no more than about 10%.

By contrast, FIG. 2 is a scanning electron micrograph of a cross-section of a film prepared according to a method of the present invention. This film has a core layer of HDPE containing about 5% CaCO₃ as a cavitant. It is clear from FIG. 2 that the cavitation introduced into the core layer includes not only the opening up in the film plane that is consistent with the cavitation observed in polypropylene, but also contains a significant and surprising degree of opening in the vertical dimension. This unexpected vertical opening in the film structure is observed to correlate with extraordinary increases in the WVTR of the core layer. It has been found that this feature of the films of the invention permits selection of a wide range of WVTR values for the film by the process of providing one or more WVTR-controlling layers to limit net WVTR for the resulting film.

EXAMPLE 2

TABLE 1 shows a film structure produced by a method of the present invention. The film has an unexpectedly high WVTR of greater than 3.0 g/100 inch²·day.

TABLE 1

| Layers (from top to bottom) | Composition of Layer | Layer Thickness(mil) |
|---|---|---|
| Outer | MDPE | 0.03 |
| Tie | MDPE | 0.10 |
| Core | HDPE + CaCO₃ | 0.89 |
| Tie | HDPE + CaCO₃ | 0.10 |
| Outer | MDPE | 0.03 |

It should be noted that the top side of this film structure is the caster side and the bottom side of the film structure is the airknife side. Also, the thickness of each layer does not account for any additional thickness resulting from cavitation.

The percentage of cavitant in the core layer and the tie layer on the airknife side of the film is about 5 to about 10% by weight of the layer. To increase the WVTR, more cavitant can be added to either or both layers containing cavitant. Additionally, cavitant can be added to the tie layer on the caster side of the film to increase the WVTR. This particular example includes MDPE in the tie layer on the caster side to reduce the WVTR.

The WVTR of a film can be increased or decreased by varying the physical conditions with respect to the film-making process. For example, reducing the thickness of non-cavitated layers increases the WVTR. Likewise, reducing the resin density of non-cavitated layers increases the WVTR of a film. The WVTR can also be increased by using lower stretch temparatures as shown in EXAMPLE 3 below or by using higher stretch ratios in the machine or transverse directions.

With respect to the resulting film of this example, the WVTR is much higher than anticipated. Other physical attributes of the film include a gloss of 25% and a light transmission ratio of 20%. The optical gauge is 2.00 mil and the polygauge is 1.15 mil.

EXAMPLE 3

The film structures described in TABLE II show that WVTR increases when stretching is performed at lower temperatures and when structures are more cavitated.

TABLE II

| Sample | Layer 1 | Layer 2 | Layer 3 | Layer 4 | Layer 5 | WVTR |
|---|---|---|---|---|---|---|
| 1 | 0.03 MDPE | 0.10 HDPE | 0.89 HDPE + 7% CaCO₃ | 0.10 HDPE | 0.03 MDPE | 1.00 |
| 2 | 0.03 MDPE | 0.10 HDPE | 0.89 HDPE + 7% CaCO₃ | 0.10 HDPE | 0.03 MDPE | 2.05 |
| 3 | 0.03 MDPE | 0.10 HDPE | 0.89 HDPE + 7% CaCO₃ | 0.10 HDPE | 0.03 MDPE | 0.88 |
| 4 | 0.03 MDPE | 0.10 MDPE | 0.89 HDPE + 7% CaCO₃ | 0.10 HDPE + 7% CaCO₃ | 0.03 MDPE | 2.93 |
| 5 | 0.03 MDPE | 0.10 HDPE | 0.89 HDPE + 7% CaCO₃ | 0.10 HDPE + 7% CaCO₃ | 0.03 MDPE + 7% CaCO₃ | 14.1 |

The thickness of the HDPE and MDPE layers is expressed above in mils not taking into account additional thickness resulting from cavitation. In addition, the WVTR is expressed above in g/100 inch²·day.

Samples 1 and 3 were produced under similar conditions to establish a constant WVTR for comparison with WVTR values resulting from different physical conditions. Comparing the WVTR of Samples 1 and 3 with that of Sample 2, it is readily apparent that a lower stretch temperature caused an increase in the WVTR of Sample 2. Sample 2 stretch temperatures were about 3° F. lower compared to Sample 1.

Sample 4 was performed at conditions similar to Sample 1 and 3 except that layer 4 of Sample 4 was cavitated. The resulting increase in WVTR in Sample 4 compared to those of Samples 1 and 3 indicates that WVTR increases as a film is more cavitated.

The result in Sample 5 further supports the assertion drawn from the comparison of Sample 4 to Samples 1 and 3. In particular, tie layers 2 and 4 of Sample 5 were cavitated and the resulting WVTR was much higher than the WVTR of Samples 1 and 3. Clearly, increasing the cavitation of a film results in higher WVTR values.

EXAMPLE 4

TABLE III shows three layer film structures resulting from process conditions different than those used in obtaining the results of TABLE II. In particular, the results of TABLE III show that WVTR increases as cavitation increases regardless of what cavitant is used.

TABLE III

| Sample | Layer 1 | Layer 2 | Layer 3 | WVTR |
|---|---|---|---|---|
| 5 | 0.17 MDPE | 0.81 HDPE (M6211 Resin) | 0.17 MDPE | 0.2 |
| 6 | 0.17 MDPE | 0.81 HDPE + 7% $CaCO_3$ | 0.17 MDPE | 4.0 |
| 7 | 0.17 MDPE | 0.81 HDPE + 7% $CaCO_3$ | 0.17 MDPE | 7.2 |
| 8 | 0.17 MDPE | 0.81 HDPE + 7% Epostar MA1002 | 0.17 MDPE | 5.2 |

The thickness of the HDPE and MDPE layers is expressed above in mils. In addition, the WVTR is expressed above in $g/100$ $inch^2 \cdot day$.

Sample 5 and Samples 6–8 can be compared to clearly prove that cavitation increases the WVTR of a film. In particular, Sample 5 which is not cavitated had a resulting WVTR of 0.2 $g/100$ $inch^2 \cdot day$ whereas Samples 6–8 which each had a cavitated core layer had resulting WVTRs of 4.0 $g/100$ $inch^2 \cdot day$, 7.2 $g/100$ $inch^2 \cdot day$, and 5.2 $g/100$ $inch^2 \cdot day$ respectively.

Sample 8 is comparable to Samples 6 and 7 to illustrate that cavitating agents other than calcium carbonate ($CaCO_3$) can be used to obtain similar results. In particular, Epostar MA 1002 was used as the cavitating agent in Sample 8. The resulting WVTR of 5.2 $g/100$ $inch^2 \cdot day$ in Sample 8 clearly supports the notion that cavitating agents other than calcium carbonate ($CaCO_3$) can be used in the methods of the present invention.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A method of producing a multilayer polyethylene film comprising the steps of:
    (i) casting a polyethylene sheet comprising:
        (a) a base layer comprising polyethylene and a cavitating agent, and
        (b) a layer of a WVTR-controlling material coextensively adherent to a side of the base layer; and
    (ii) biaxially orienting said polyethylene sheet resulting from step (i) to obtain a WVTR of greater than 0.2 $g/100$ $inch^2 \cdot day$ in the multilayer polyethylene film; wherein the base layer has a porous microstructure and a WVTR higher than the WVTR of the multilayer polyethylene film.

2. A method according to claim 1, wherein the polyethylene is a medium density polyethylene (MDPE) or a high density polyethylene (HDPE).

3. A method according to claim 1, wherein the WVTR-controlling material is a medium density polyethylene (MDPE) or a high density polyethylene (HDPE) having a density no greater than that of the polyethylene in the base layer.

4. A method according to claim 1, wherein the cavitating agent comprises a material selected from the group consisting of calcium carbonate ($CaCO_3$), polystyrene, and mixtures thereof.

5. A method according to claim 1, wherein the WVTR-controlling material is provided in an amount sufficient to yield a WVTR-controlling layer in the film having a thickness of from about 0.03 mil (3 gauge) to about 0.15 mil (15 gauge).

6. A method according to claim 1, wherein the polyethylene in the base layer is provided in an amount sufficient to yield a base layer in the film having a thickness of from about 0.5 mil (50 gauge) to about 2.0 mil (200 gauge).

7. A method according to claim 1, wherein the casting step comprises casting a sheet having first and second layers of a WVTR-controlling material coextensively adherent to first and second sides of the base layer.

8. A method according to claim 7, wherein the casting step comprises providing:
    a first tie layer interposed between the base layer and the first WVTR-controlling layer, coextensively adherent to each of the base layer and the WVTR-controlling layer, and
    a second tie layer interposed between the base layer and the second WVTR-controlling layer, coextensively adherent to each of the base layer and the WVTR-controlling layer.

9. A method according to claim 1, wherein the casting step comprises providing at least one tie layer interposed between the base layer and the WVTR-controlling layer and coextensively adherent to each of the base layer and the WVTR-controlling layer.

10. A method according to claim 9, wherein each WVTR-controlling layer comprises an ethylene-propylene copolymer or an ethylene-propylene-butylene terpolymer, and each tie layer comprises a low density polyethylene (LDPE) or an MDPE.

11. A method according to claim 1, wherein the polyethylene in the base layer is provided in an amount sufficient to yield a base layer in the film having a thickness from about 0.85 mil (85 gauge) to about 1.10 mil (110 gauge).

* * * * *